(12) United States Patent
Halm

(10) Patent No.: US 10,881,810 B2
(45) Date of Patent: Jan. 5, 2021

(54) DRUG DELIVERY DEVICE WITH A CAP

(71) Applicant: Sanofi-Aventis Deutschland GMBH, Frankfurt am Main (DE)

(72) Inventor: Markus Halm, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 240 days.

(21) Appl. No.: 15/778,501

(22) PCT Filed: Nov. 21, 2016

(86) PCT No.: PCT/EP2016/078275
§ 371 (c)(1),
(2) Date: May 23, 2018

(87) PCT Pub. No.: WO2017/089285
PCT Pub. Date: Jun. 1, 2017

(65) Prior Publication Data
US 2018/0344943 A1    Dec. 6, 2018

(30) Foreign Application Priority Data

Nov. 27, 2015 (EP) .................................... 15196710

(51) Int. Cl.
*A61M 5/32* (2006.01)
*A61M 5/24* (2006.01)

(52) U.S. Cl.
CPC ............ *A61M 5/3202* (2013.01); *A61M 5/24* (2013.01); *A61M 5/2466* (2013.01); *A61M 2005/2474* (2013.01)

(58) Field of Classification Search
CPC ...... A61M 5/3202; A61M 5/321; A61M 5/24; A61M 5/2033; A61M 5/20; A61M 5/347;
(Continued)

(56) References Cited

U.S. PATENT DOCUMENTS 3,825,003 A * 7/1974 Kruck .................. A61M 5/288
604/192
10,201,659 B2  2/2019 Kaufmann et al.
(Continued)

FOREIGN PATENT DOCUMENTS

WO    WO 2011/112136    9/2011
WO    WO 2013/063707    5/2013
WO    WO 2015/117854    8/2015

OTHER PUBLICATIONS

PCT International Preliminary Report on Patentability in International Appln. No. PCT/EP2016/078275, dated May 29, 2018, 7 pages.
(Continued)

*Primary Examiner* — Kami A Bosworth
*Assistant Examiner* — Antarius S Daniel
(74) *Attorney, Agent, or Firm* — Fish & Richardson P.C.

(57) ABSTRACT

A drug delivery device comprises a cap releasably secured to a main body of the drug delivery device and a needle assembly retained within the cap. The drug deliver device also includes a pre-stressed biasing element disposed between the cap and the needle assembly and configured to bias the needle assembly in a distal direction with respect to the drug delivery device while the cap is secured to the main body. The drug delivery device further comprises one or more locking elements each having a locked position and an unlocked position. In the locked position, the locking elements prevent the needle assembly from engaging with a cartridge retained within the main body. In an initial position, the cap is configured to retain the locking elements in the locked position. In an intermediate position, the cap is configured to release the locking elements to allow the needle assembly to engage with the cartridge.

15 Claims, 5 Drawing Sheets

(58) Field of Classification Search
CPC ...... A61M 5/344; A61M 5/34; A61M 5/2455; A61M 5/3213; A61M 5/3216; A61M 2005/1585; A61M 2005/206; A61M 2005/2474; A61M 2005/312
See application file for complete search history.

(56) References Cited

U.S. PATENT DOCUMENTS

| | | | | |
|---|---|---|---|---|
| 2008/0269690 | A1* | 10/2008 | Felix-Faure | A61M 5/3202 604/192 |
| 2014/0025014 | A1* | 1/2014 | Radmer | A61M 5/002 604/198 |
| 2016/0250421 | A1* | 9/2016 | Fincham | A61M 5/3202 604/198 |

OTHER PUBLICATIONS

PCT International Search Report and Written Opinion in International Appln. No. PCT/EP2016/078275, dated Jan. 11, 2017, 9 pages.

* cited by examiner

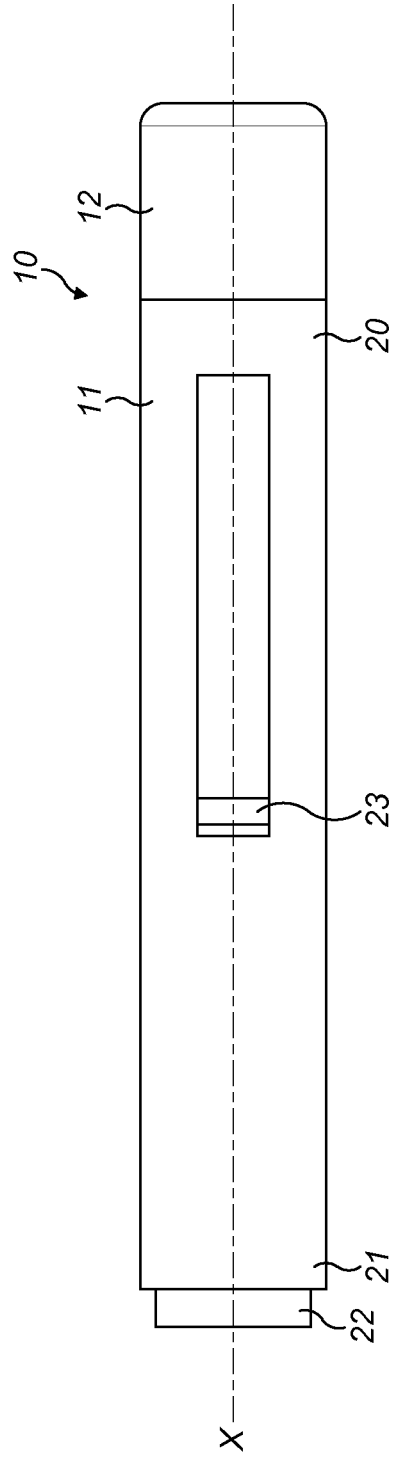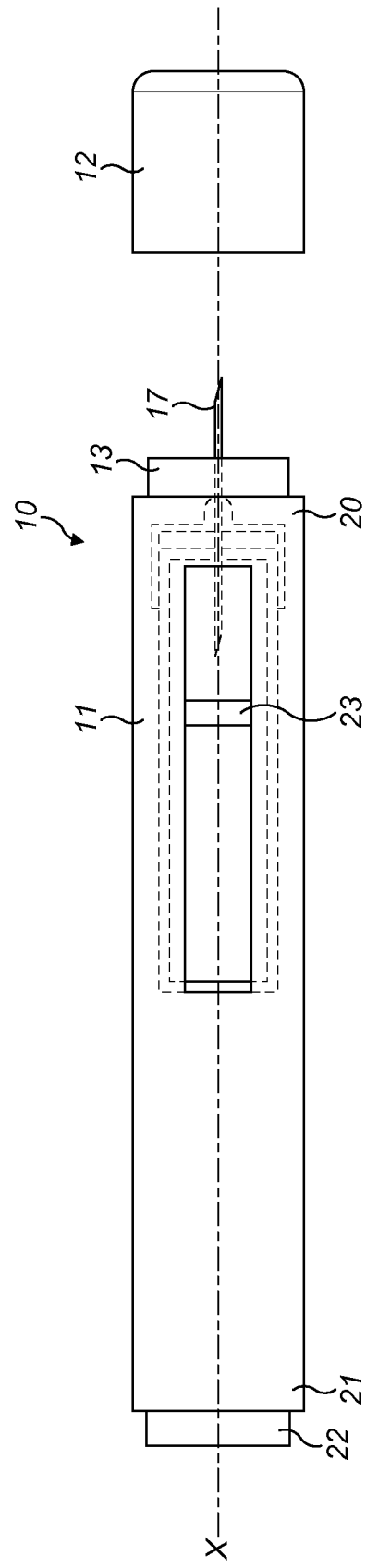

DRUG DELIVERY DEVICE WITH A CAP

CROSS REFERENCE TO RELATED APPLICATIONS

This application is a U.S. national stage application under 35 USC § 371 of International Application No. PCT/EP2016/078275, filed on Nov. 21, 2016, which claims priority to European Application No. 15196710.6, filed on Nov. 27, 2015, the entire contents of which are incorporated herein by reference.

TECHNICAL FIELD

The present disclosure relates to a drug delivery device having a cap.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Other types of disease require injections using auto-injectors. These injections may be weekly or every two or four weeks.

SUMMARY

An aspect of the specification provides a drug delivery device comprises a cap releasably secured to a main body of the drug delivery device; a needle assembly retained within the cap; a pre-stressed biasing element disposed between the cap and the needle assembly and configured to bias the needle assembly in a distal direction with respect to the drug delivery device while the cap is secured to the main body; and one or more locking elements each having a locked position and an unlocked position, wherein in the locked position the locking elements prevent the needle assembly from engaging with a cartridge retained within the main body, wherein the cap is configured in an initial position to retain the locking elements in the locked position and in an intermediate position to release the locking elements to allow the needle assembly to engage with the cartridge.

The cap may be secured to the drug delivery device in the initial position and in the intermediate position and is unsecured from the drug delivery device in a final position.

Each of the locking elements may comprise a locking member and a biasing member configured to bias the locking member towards the unlocked position. Here, the biasing member may be disposed between the locking member and a main body of the drug delivery device.

The pre-stressed biasing element may be configured to force the needle assembly to move axially within the integrated cap assembly after the cap has been moved from the initial position to the intermediate position, such that the needle assembly contacts a cartridge retained within the main body of the drug delivery device.

The needle assembly may be configured to abut the locking members when the locking members are in the locked position.

The cap may be releasably secured to the main body of the drug delivery device by a bayonet fitting.

The cap may be configured to be moved from the initial position to the intermediate position and from the intermediate position to the final positions by rotation.

A proximal end of the needle assembly may be covered by a pierceable seal.

The drug delivery device may further comprise a cartridge holder and one or more cutting elements supported on a distal end of the cartridge holder, the cutting elements arranged to pierce the pierceable seal when the needle assembly contacts the cartridge holder. Here, the needle assembly may comprise an outer needle shield and inner needle shield and removal of the cap from the drug delivery device may also remove the outer needle shield, and optionally the outer needle shield may comprise one or more resiliently deformable clips configured to allow the outer needle shield to be secured axially within the needle assembly.

The needle assembly may further comprise a needle supported by a needle holder. The needle holder may be retained within the outer needle shield. The needle holder may be configured to engage via a friction or a threaded connection with the cartridge holder in order to secure the needle to the cartridge.

The drug delivery device may further comprise a medicament contained within the cartridge.

Another aspect of the specification comprises a cap for a drug delivery device, the cap comprising a needle assembly retained within the cap; and a pre-stressed biasing element disposed between the cap and the needle assembly and configured to bias the needle assembly distally with respect to the drug delivery device while the cap is secured to a main body of a drug delivery device; wherein the cap is configured in an initial position to retain locking elements of the cap or the main body in a locked position and in an intermediate position to release the locking elements to allow the needle assembly to engage with a cartridge located within the main body of the drug delivery device.

A further aspect of the specification provides a method relating to a drug delivery device, the method comprising rotating a cap relative to a main body to move one or more locking elements; upon rotation resulting in unlocking of the one or more unlocking elements, a biasing element being released; and release of the biasing element causing a needle assembly contained within the cap to engage with a cartridge contained within the main body.

The terms "drug" or "medicament" which are used interchangeably herein, mean a pharmaceutical formulation that includes at least one pharmaceutically active compound.

The term "drug delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, exemplary injection devices may include, e.g., syringes, autoinjectors, injection pen devices and spinal injection systems.

Due to the physical impairment of some users, it is desirable to keep the user interaction required to prepare and operate the injection pen simple and minimal.

These and other aspects will be apparent from and elucidated with reference to the embodiments described hereinafter.

BRIEF DESCRIPTION OF THE DRAWINGS

Exemplary embodiments of the present invention are described with reference to the accompanying drawings, in which:

FIG. 1A is a schematic side view of an injection device according to an exemplary embodiment, with a cap attached to a body of the injection device;

FIG. 1B is a schematic side view of the injection device of FIG. 1A, with the cap removed from the body;

DETAILED DESCRIPTION

Figure 2:
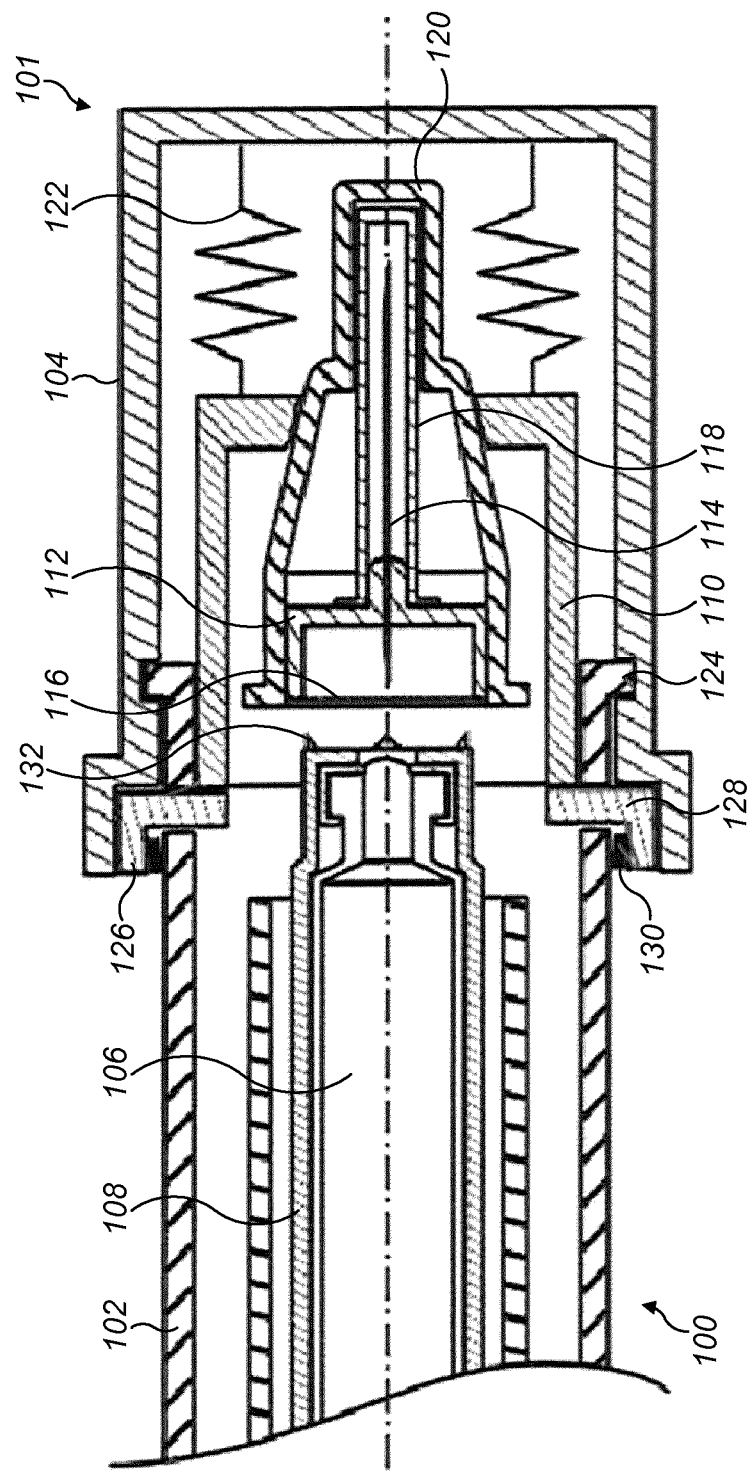
FIG. 2 is a cut-through view of a drug delivery device and integrated cap assembly according to exemplary embodiments in an initial position.

One or more embodiments provide an arrangement with a mechanism by which twisting of a cap by a user relative to a main body of a drug delivery device causes a needle assembly to be moved towards and then engaged with a medicament cartridge. The mechanism also causes an outer needle shield to be detached from the needle assembly, allowing the cap and the outer needle shield to be removed from the main body whilst leaving the needle assembly engaged with the medicament cartridge. Thus, fitting of the needle assembly onto the medicament cartridge and removal of the cap can be achieved in a relatively small number of steps.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 gauge in size. Common sizes are 27 and 29 gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Referring now to FIG. 2, a drug delivery device 100 according to exemplary embodiments is shown. The drug delivery device 100 is an embodiment of the device 10 of FIGS. 1A and 1B. The drug delivery device 100 has a main body 102 (corresponding to the housing 11 of FIGS. 1A and 1B), which retains the other elements of the drug delivery device. The drug delivery device 100 also has an integrated cap assembly 101 releasably mounted thereto. The integrated cap assembly 101 comprises a cap 104 (corresponding to the cap 12 of FIGS. 1A and 1B) which is releasable secured to the main body 102 and which retains the other elements of the integrated cap assembly. The drug delivery device 100 houses a medicament cartridge 106. The cartridge 106 may be retained in a cartridge holder 108.

The integrated cap assembly 101 houses a needle assembly 110. The needle assembly 110 comprises a needle holder 112 supporting a double-ended needle 114 (corresponding to the needle 17 of FIGS. 1A and 1B). The proximal end of the needle holder 112 is covered by a pierceable seal 116. The distal end of the needle holder 112 is engaged by an inner needle shield 118, which covers the distal end of the double-ended needle 114. The needle holder 112 and inner needle shield 118 are both covered by an outer shield 120. The outer shield 120 is secured to or may be integral with the needle assembly 110. The integrated cap assembly 101 also comprises a pre-stressed biasing element 122 disposed between the cap 104 and the needle assembly 110. The pre-stressed biasing element 122 may be a pre-compressed spring. The pre-stressed biasing element 122 biases the cap 104 and needle assembly apart.

The cap 104 comprises engaging features or generally engaging means for releasable securing the integrated cap assembly 101 to the drug delivery device 100. These engaging features may comprise one or more grooves in the inner surface of the cap 104, which form a bayonet type fitting. The main body 102 of the drug delivery device 100 may comprise corresponding protrusions 124, which engage with the grooves.

The drug delivery device 100 further comprises one or more locking elements 126. The locking elements 126 are configured to prevent the needle assembly 110 from engaging with the medicament cartridge 106 when in the locked position and to allow the needle assembly to engage with the cartridge when in the unlocked position. Each of the one or more locking elements 126 may comprise a locking member 128 and a biasing member 130, which acts between the locking member 128 and main body 102 of the drug delivery device to bias these components apart. Each of the biasing members 130 may be a pre-compressed spring. Each of the locking members 128 may be configured to move radially with respect to the main body 102 of the drug delivery device.

The cartridge holder 108 has at its distal end one or more cutting elements 132 configured to pierce the seal 116 of the needle holder 112 when the needle assembly 110 is forced against the cartridge holder.

FIG. 2 shows the drug delivery device and integrated cap assembly 101 in an initial position (or initial rotational position). In this position, one or more proximal protrusions on the cap 104 engage the locking elements 126 and retain them in the locked position. The proximal end of the needle assembly 110 abuts the locking members 128 of the locking elements 126, which prevents the needle assembly 110 from engaging with the cartridge 106.

Figure 3:
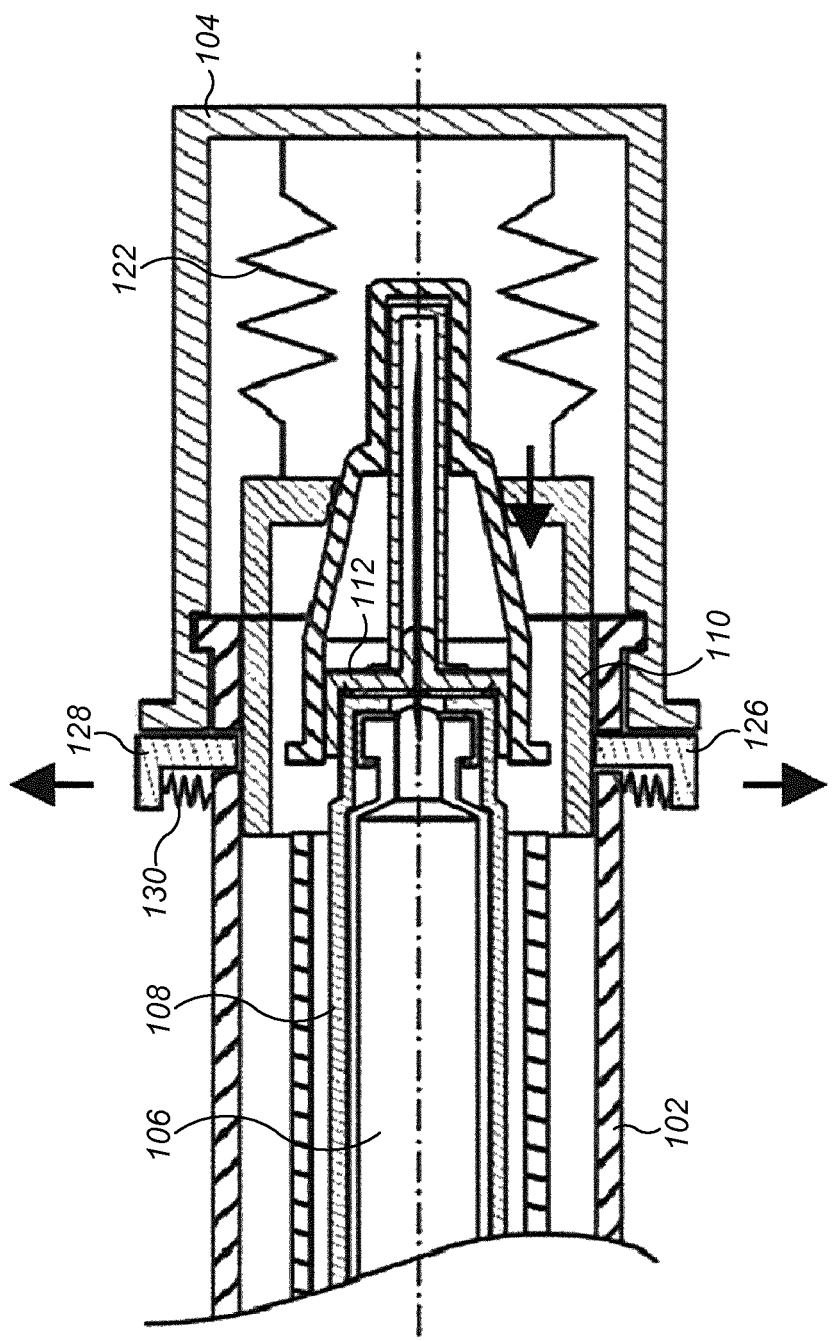
FIG. 3 is a cut-through view of a drug delivery device and integrated cap assembly according to exemplary embodiments in an intermediate position

In use, a user grasps the cap 104 when it is in the initial position shown in FIG. 2 and rotates it relative to the main body 102 of the drug delivery device. Referring also now to FIG. 3, as the user rotates the cap 104, the proximal protrusions of the cap 104 are rotated away from the locking members 128 such that they no longer engage the locking member 128. As the locking members 128 are biased radially outwards by the biasing members 130, once the locking members 128 are no longer retained by the cap 104, the locking elements 126 move from the locked position to an unlocked position, as indicated by the arrows in FIG. 3. FIG. 3 therefore shows the integrated cap assembly 101 in an intermediate position (or intermediate rotational position).

When the locking elements 126 are in the unlocked position, they no longer restrain the needle assembly 110. The needle assembly 110 is then free to move proximally under force from the pre-stressed biasing element 122, as indicated by the arrow in FIG. 3. As the needle assembly 110 moves proximally, the cutting elements 132 on the cartridge holder 108 contact the pierceable seal 116, causing it to tear. The proximal end of the needle 114 is then forced through the septum of the cartridge 106 and enters the medicament chamber of the cartridge. The proximal end of the needle 114 may also pierce the seal 116. The needle assembly 110 stops moving proximally when the needle holder 112 abuts the cartridge holder 108. Thus, the attachment of the needle 114 to the cartridge 106 is achieved automatically during user removal of the cap 104 from the distal end of the main body 102 (although it may remain tethered thereto). This is advantageous as it may reduce the number of separate steps required by the user to properly prepare the device for an injection process.

Figure 4:
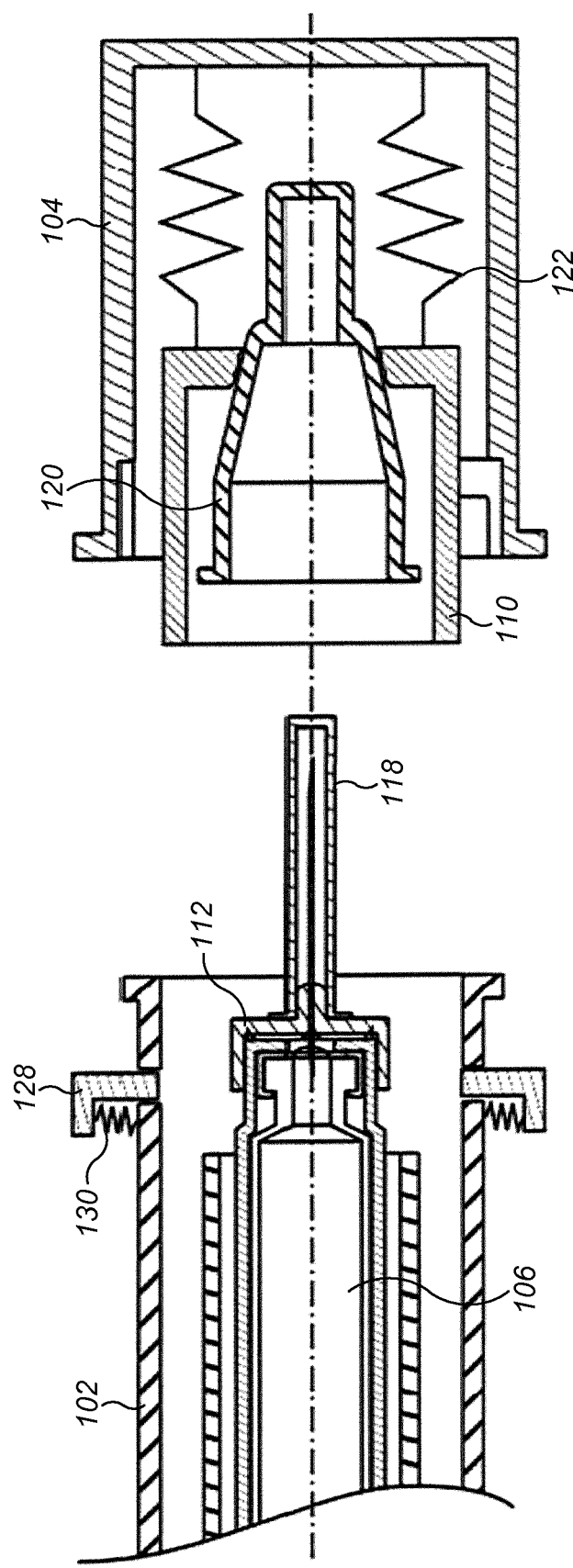
FIG. 4 is a cut-through view of a drug delivery device and integrated cap assembly according to exemplary embodiments in a final position

The user continues to rotate cap 104 until the protrusions 124 on the main body 102 reach the end of the bayonet fitting grooves in the cap. The bayonet slot in the cap 104 can most clearly be seen in FIG. 4. In this final position, the cap 104 is free to be pulled away and removed from the main body 102 of the drug delivery device 100, as shown in FIG. 4. As can be seen in FIG. 4, as the needle assembly 110 is secured to the cap via the pre-stressed biasing element 122 and the outer shield 120 is secured to or integral with the needle assembly 110, these elements are removed with the cap 104. The inner needle shield 118 remains secured to the needle holder 112 as the cap 104 is removed. The user then removes the inner needle shield 118 in order to expose the needle 114 and perform a medicament injection process. Thus, the user is able to prepare the drug delivery device for injection in a process requiring only two steps. First, the user rotates and removes the cap 104, causing the needle assembly to be released and the cartridge pierced. Then the inner needle shield 118 is removed to expose the needle.

The needle holder 112 may be secured to the cartridge holder 108 by a friction connection. The presence of the needle 114 in the septum of the cartridge 106 may increase the quality of this friction connection. Furthermore, the inner surface of the needle holder 112 may comprise a relatively soft plastic, and the cutting element 132 on the distal end of the cartridge holder 108 may be embedded in this material under the force from the pre-stressed biasing element 122. Alternatively, the inner surface of the needle holder 112 and outer surface of the cartridge holder 108 may be provided with corresponding threads. A mechanism (not shown) may be provided to cause or allow rotation of either or both of the cartridge holder 108 and the needle holder 112 to cause the corresponding threads to engage.

Figure 5:
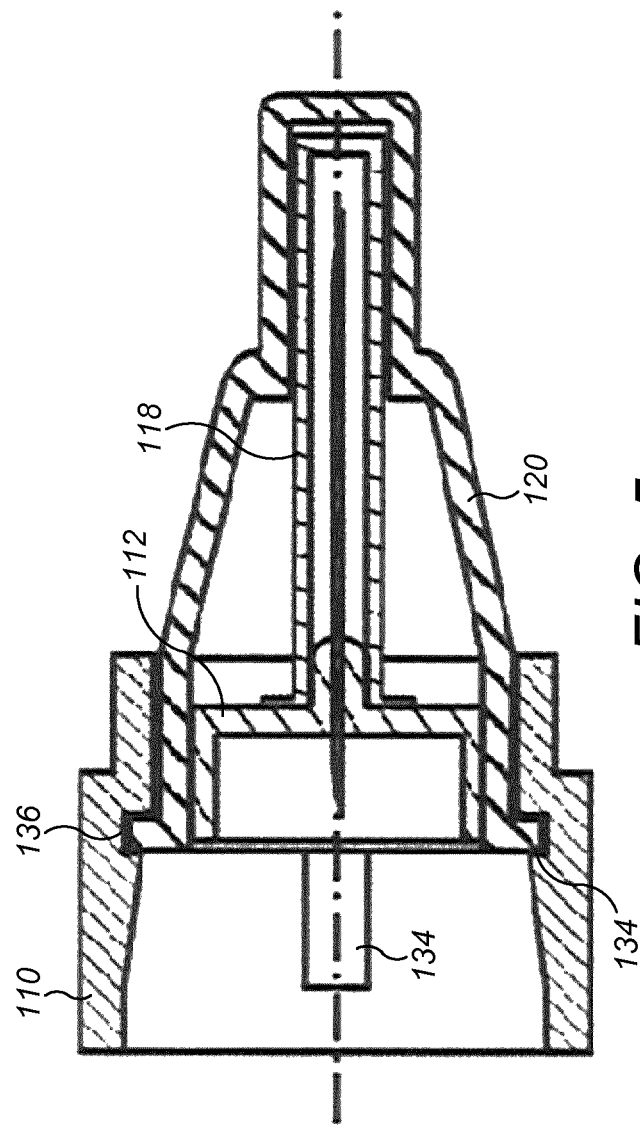
FIG. 5 is a cut-through view of some component of the integrated cap assembly of FIGS. 2 to 4.

FIG. 5 illustrates one exemplary way in which the outer shield 120 may be secured to the needle assembly 110. The pre-stressed biasing element 122 and cap 104 are omitted from FIG. 5 for clarity. The outer shield 120 comprises one or more clips 134 at its proximal end, which are received in one or more corresponding recesses 136 in the needle assembly 110. This configuration may aid in manufacture of the integrated cap assembly 101. For example, the outer shield 120 may first be inserted from the proximal end of the needle assembly 110. The outer shield 120 is preferably made from a slightly resilient material, such as a plastic. As the inner diameter of the needle assembly 110 tapers inwards, the proximal end of the outer shield 120 is deformed until the clips 134 engage with the recesses 136. The outer shield 120 is then secured and cannot move axially in either direction. The needle holder 112 may then be inserted from the proximal end into the outer shield 120. The pierceable seal 116 may be attached to the needle holder 112 before or after its insertion into the outer shield 120. The assembly as shown in FIG. 5 may then be secured within the cap 104. The pre-stressed biasing element 122 may be secured to the needle assembly 110 and stressed as the cap 104 is attached to the drug delivery device 100. Thus, the described arrangement of component allows for an apparatus which is both easy to manufacture and which requires minimal separate user steps to activate.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastrointestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 68° F. (20° C.)), or refrigerated temperatures (e.g., from about 25° F. (−4° C.) to about 39° F. (4° C.)). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminogly-cane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. A drug delivery device comprising:
    a cap releasably secured to a main body of the drug delivery device;
    a needle assembly retained within the cap;
    a pre-stressed biasing element disposed between the cap and the needle assembly and configured to bias the needle assembly in a proximal direction with respect to the drug delivery device while the cap is secured to the main body; and
    one or more locking elements, wherein:
        each of the one or more locking elements comprises a locking member having a locked position and an unlocked position, and a biasing member configured to bias the locking member towards the unlocked position; and
        in the locked position, the one or more locking elements prevent the needle assembly from engaging with a cartridge retained within the main body,
    wherein the cap is configured in an initial position to retain the one or more locking members in the locked position and in an intermediate position to release the one or more locking elements to allow the needle assembly to engage with the cartridge.

2. The drug delivery device according to claim 1, wherein the cap is secured to the main body of the drug delivery device in the initial position and in the intermediate position and is unsecured from the main body of the drug delivery device in a final position.

3. The drug delivery device according to claim 1, wherein, for each of the one or more locking elements, the biasing member is disposed between the locking member and the main body of the drug delivery device.

4. The drug delivery device according to claim 1, wherein the needle assembly is configured to abut the locking member of each of the one or more locking elements when the locking member is in the locked position.

5. The drug delivery device according to claim 1, wherein the pre-stressed biasing element is configured to force the needle assembly to move axially within the cap after the cap has been moved from the initial position to the intermediate position, such that the needle assembly contacts the cartridge retained within the main body of the drug delivery device.

6. The drug delivery device according to claim 1, wherein the cap is releasably secured to the main body of the drug delivery device by a bayonet fitting.

7. The drug delivery device according to claim 1, wherein the cap is configured to be moved from the initial position to the intermediate position and from the intermediate position to a final position by rotation; and wherein the cap is unsecured from the main body of the drug delivery device in the final position.

8. The drug delivery device according to claim 1, wherein a proximal end of the needle assembly is covered by a pierceable seal.

9. The drug delivery device according to claim 8 further comprising a cartridge holder and one or more cutting elements supported on a distal end of the cartridge holder, the one or more cutting elements arranged to pierce the pierceable seal when the needle assembly contacts the cartridge holder.

10. The drug delivery device according to claim 1, wherein the needle assembly comprises an outer needle shield and an inner needle shield, and wherein removal of the cap from the main body of the drug delivery device also removes the outer needle shield.

11. The drug delivery device of claim 10, wherein the outer needle shield comprises one or more resiliently deformable clips configured to allow the outer needle shield to be secured axially within the needle assembly.

12. The drug delivery device according to claim 10, wherein the needle assembly further comprises a needle supported by a needle holder, the needle holder retained within the outer needle shield, the needle holder configured to engage via a friction or a threaded connection with a cartridge holder in order to secure the needle to the cartridge.

13. The drug delivery device according to claim 1, further comprising a medicament contained within the cartridge.

14. A system comprising an integrated cap assembly and a drug delivery device, the integrated cap assembly comprising:
    a cap
    a needle assembly retained within the integrated cap assembly; and
    a pre-stressed biasing element disposed between the cap and the needle assembly and configured to bias the needle assembly proximally with respect to the drug delivery device while the cap is secured to a main body of the drug delivery device; and
    the drug delivery device comprising:
        one or more locking elements, each of the one or more locking elements comprising a locking member having a locked position and an unlocked position, and a biasing member configured to bias the locking member towards the unlocked position;
        wherein the cap is configured in an initial position to retain the one or more locking members in the locked position and in an intermediate position to release the one or more locking elements to allow the needle assembly to engage with a cartridge located within the main body of the drug delivery device.

15. A method relating to a drug delivery device, the method comprising:
    rotating a cap relative to a main body to move one or more locking elements, each of the one or more locking elements comprising a locking member having a locked position and an unlocked position, and a biasing member configured to bias the locking member towards the unlocked position;

upon rotation resulting in unlocking of the one or more locking elements from a needle assembly contained within the cap, a biasing element being released; and release of the biasing element causing the needle assembly contained within the cap to engage with a cartridge contained within the main body.

* * * * *